United States Patent [19]

Dixon et al.

[11] Patent Number: 5,736,631
[45] Date of Patent: Apr. 7, 1998

[54] TURF IMPACT ANALYSIS SYSTEM

[75] Inventors: Charles R. Dixon, Olathe; Stephen B. McWilliams, Leawood, both of Kans.

[73] Assignee: Turf Diagnostics & Design, Inc., Olathe, Kans.

[21] Appl. No.: 613,356

[22] Filed: Mar. 11, 1996

[51] Int. Cl.$^6$ .............................. G01N 3/30; G01M 7/00
[52] U.S. Cl. .......................................... 73/12.06; 73/12.13
[58] Field of Search .............................. 73/12.01, 12.14, 73/12.04, 12.06, 12.09, 12.13, 12.07

[56] References Cited

U.S. PATENT DOCUMENTS

| | | | |
|---|---|---|---|
| 4,055,842 | 10/1977 | Yakshin et al. | 73/12.01 |
| 4,180,892 | 1/1980 | Jensen . | |
| 4,189,655 | 2/1980 | Bruel . | |
| 4,211,951 | 7/1980 | Jensen . | |
| 4,493,063 | 1/1985 | Yims et al. | 73/1 DV |
| 4,620,446 | 11/1986 | Jensen et al. . | |
| 4,711,754 | 12/1987 | Bednar | 73/12.09 |
| 5,353,233 | 10/1994 | Oian et al. . | |
| 5,400,297 | 3/1995 | Frederiksen . | |
| 5,490,411 | 2/1996 | Hogan | 73/12.01 |

OTHER PUBLICATIONS

Clegg, B., "An Impact Testing Device For In Situ Base Course Evaluation", ARRB Proceedings, vol. 8, 1976.

Clegg, B., "Field Assessment of the Impact Soil Tester", ARRB Research Report ARR No. 76, Australian Road Research Board, Vermont South, Victoria, Aug. 1977.

Clegg, B., "An Impact Soil Test for Low Cost Roads", Proceedings of 2nd Conference of Road Engineers Association of Asia & Australia, Manila, Oct. 1978.

Granelli, U. "Materials Testing in the Design and Construction of Flexible Road Bases", Le Strade, anno LXXXV, n 1206, gennaio–febbraio 1983.

Clegg, B., "Design Compatible Control of Basecourse Construction", Australian Road Research 13(2), Jun. 1983.

Rogers, J.N. III and Waddington, D.V., "Portable Apparatus for Assessing Impact Characteristics of Athletic Field Surfaces", *Natural and Artificial Playing Fields: Characteristics and Safety Features, ASTM STP 1073*, no date.

Bregar, M.J. and Moyer, W.W., "An Automated System for Field Testing and Soil Impact Analysis", *Natural and Artificial Playing Fields: Characteristics and Safety Features, ASTM STP 1073*, R.C. Schmidt, E. F. Hoerner, E.M. Milner, and C.A. Morehouse, Eds., American Society For Testing and Materials, Philadelphia 1990, pp. 115–126.

"NI–DAQ User Manual for PC Compatibles", National Instruments Corporation, Austin, TX, Sep. 1994, pp. 1–4, 1–5, 1–11, and 2–1.

"Impact Soil Tester" brochure, Lafayette Instrument Company, Lafayette, IN, (date unknown).

*Primary Examiner*—Ronald L. Biegel
*Assistant Examiner*—Max H. Noori
*Attorney, Agent, or Firm*—Litman, McMahon & Brown, L.L.C.

[57] ABSTRACT

A system for impact analysis of soil surfaces includes a Clegg impact hammer, an accelerometer mounted on the hammer, an analog to digital converter to digitize the deceleration signal of the accelerometer, and a computer to store the digitized curve samples and to calculate selected impact parameters from the curve samples. The apparatus includes a notebook computer and additional components all of which are portable to enable storage of a great number of curve samples and calculation of the impact parameters for a large number of test points in the field immediately after each hammer drop.

4 Claims, 2 Drawing Sheets

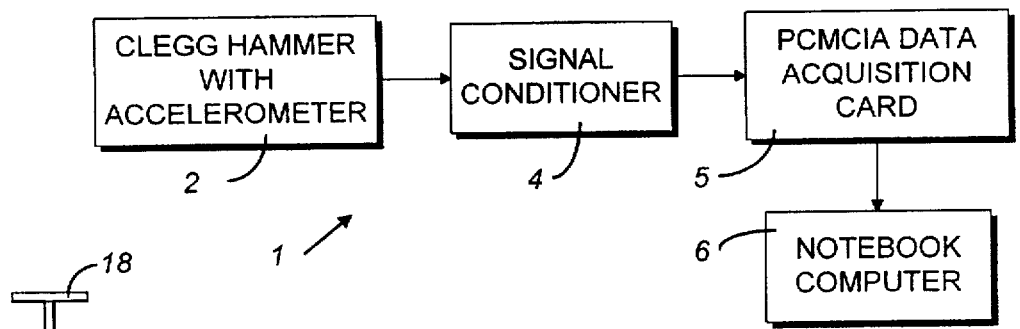
FIG. 1.
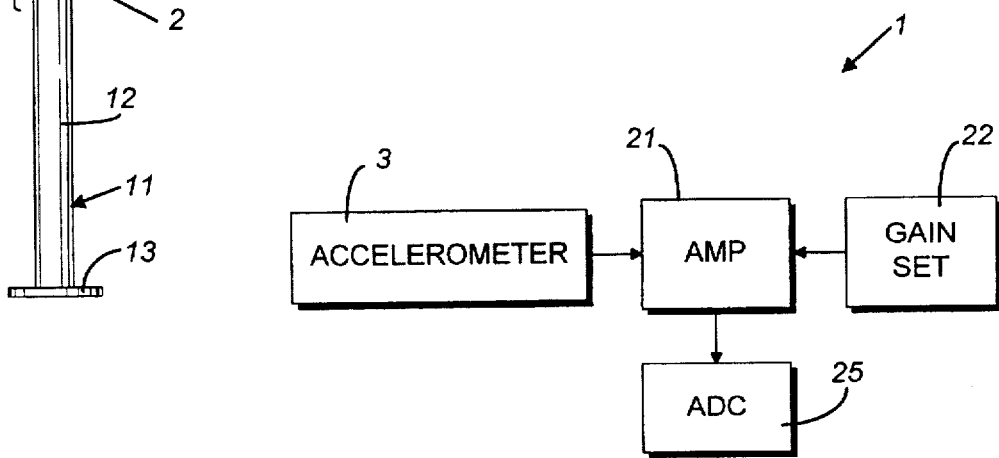
FIG. 2.
FIG. 3.
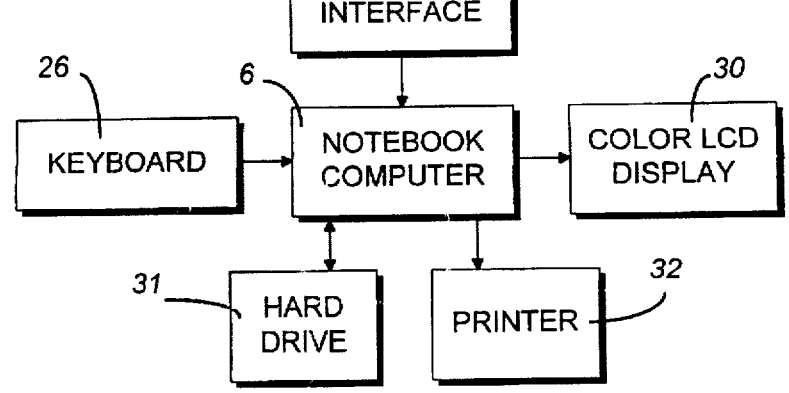

TURF IMPACT ANALYSIS SYSTEM

BACKGROUND OF THE INVENTION

The surface condition of the ground is important in a number of areas. In roadbuilding and in building construction, a stable, compacted soil condition is desirable so that the roadbed or structures built thereon are also stable. On playing fields where athletic contests are held, a surface condition which is too soft can cause excessive fatiguing of the athletes' legs while too hard a surface can exacerbate injuries from ground contact, particularly in contact sports. The field surface condition also affects the manner in which balls bounce.

Early work to quantitatively analyze soil surface conditions was done by Dr. Baden Clegg during the 1970's in Australia, initially in the context of roadbuilding. Clegg developed an instrument referred to as the Clegg impact Tester or Clegg "hammer", which is now widely used in such analyses. The Clegg hammer is formed by a cylindrical mass having an accelerometer mounted therein with a shaft extending upwardly from the hammer body and terminating in a handle. A cylindrical guide tube has a base flange to render the tube self-standing. The hammer body has a standard mass and is dropped through the guide tube from a standard height, in order to generate data which is comparable from analysis to analysis. While the term "standard" is used for the mass of the hammer body and the drop height, there are apparently a number of standards in use such that not all data from such analyses are directly comparable.

In the earlier Clegg hammer apparatus, the accelerometer is connected to an instrument which detects and reads out the maximum deceleration experienced by the accelerometer, which is referred to as $G_{max}$ or G-max. While the peak deceleration is an important parameter, it is known that additional parameters, which can be measured or calculated from the accelerometer output signal, provide more complete information about the character of the soil surface. These include the total duration of the impact, the time to reach maximum deceleration, the average deceleration, the rate of change of deceleration at certain stages, the area under the curve of deceleration versus time or severity index, the peak force, the deformation of the surface, and the time for the surface to return to its original state or rebounding time.

In order to measure and/or calculate such additional parameters, it is necessary to analyze the deceleration curve over time. To accomplish this, engineers have used a Bruel and Kjaer BK-2515 vibration analyzer (Bruel and Kjaer Instruments, Marlborough, Mass.) in combination with a Clegg hammer (Lafayette instrument Co., Lafayette, Ind.). The BK-2515 vibration analyzer is a battery powered, portable instrument weighing about 16.2 kg, having a display for the deceleration-time curve, an averaging capability, memory capacity to store up to fifty curves, and the ability to interface with a computer for downloading and further analysis of the curves.

Although the BK-2515 is considered portable, it is a considerable weight to move about a field under analysis. Additionally, because of its limited memory capacity and limited processing capability, it is necessary to periodically return it to a facility where its memory contents can be uploaded into a computer for a complete analysis of the curves gathered. The limitations of the BK-2515 require that impact testing of a field be well planned and executed to make the best use of the limited data points gathered. For this reason, the great majority of field surface testing operations still make use of a Clegg hammer in combination with a handheld instrument which only displays peak deceleration which is manually recorded.

SUMMARY OF THE INVENTION

The present invention provides a truly portable apparatus for impact testing of soil surfaces which can record practically an unlimited number of test impact curves and generate and store a full set of impact parameters for each deceleration curve immediately after the impact occurs, in the field. The turf impact analysis system of the present invention employs a Clegg hammer having a piezoelectric accelerometer mounted therein and connected through signal conditioner circuitry to a data acquisition circuit interfaced to a notebook sized computer.

The signal conditioner circuitry includes an active filter having several gain settings which can be selected according to the nature of the turf being tested. The signal conditioner circuitry improves the signal to noise ratio of the accelerometer signal and removes noise therefrom. The data acquisition circuit includes an analog to digital converter (ADC) along with timing circuitry which controls the sampling window of the ADC. The data acquisition circuit is in the form of a standard PCMCIA card which is received in a PCMCIA socket of the notebook computer. The computer is a battery powered portable computer having an LCD display, preferably color, which closes over the keyboard, a hard disk drive of at least several hundred megabytes, at least four to eight megabytes of RAM, and preferably a 486 or faster microprocessor. Such computers of small dimensions and having a displays which fold over their keyboards are referred to as notebook computers when their total weight including battery is about seven pounds or less.

In the present invention, a field to be analyzed is divided into a two dimensional array of grid squares, each having unique grid coordinates. The computer executes a turf analysis program which presents a display of a data record form with data fields for the entry of data describing the mass of the Clegg hammer employed, the gain setting of the signal conditioner, a time delay between a ready signal from the operator and the opening of the sampling window of the data acquisition circuit, and a comment field for entry of information identifying the testing site and grid coordinates of the field being tested and other comments. The operator raises the hammer to a standard height, gives the ready command, waits for an audible drop signal, and drops the hammer upon hearing the drop signal.

During the sampling window, the ADC sequentially samples the accelerometer signal and converts analog values of voltage to binary values which are transferred to and stored in the computer memory. An audible signal indicates that the sample window has closed. The sampling window may be a preset length of time or may be controlled by detecting selected threshold values of the accelerometer signal, Once the sampling window has ended, the program measures and/or calculates a number of impact parameters from the deceleration curve data, displays the values of the parameters, and displays the deceleration curve versus time. The calculation of the parameters is virtually immediate. Further comments can be entered into a comment field for the position being tested. The parameters and deceleration curve data can then be saved to the hard disk as a data record of a data base for the field under analysis. The displayed data record form is then cleared to prepare for another impact hammer drop, and the process can be repeated on the same grid square or on the next grid square. It is known that sequential impacts on a given spot can result in variations in the values of the impact parameters, and it might be desirable to measure such variations by repeated impact testing at the same location.

Once all the required data records have been generated, the stored records can be recalled and processed by other software for printing in hard copy, for graphing, or for other purposes, such as the generation of graphic displays of positional values of selected parameters of the field tested. The data can then be used by owners or operators of the field to correct undesirable characteristics of the field using conventional turf management techniques, such as sodding, aeration, compacting, or the like. The data base for a field which is stored in the computer can be offloaded intact to another medium for archiving or for transfer to another computer.

OBJECTS AND ADVANTAGES OF THE INVENTION

The principal objects of the present invention are: to provide an improved system for quantitative testing of the mechanical properties of soil surface conditions; to provide such a system which is convenient to move about a test site and which is capable of generating a full range of parameters describing the soil surface or turf under analysis; to provide such a system including a Clegg hammer having a piezoelectric accelerometer mounted therein, a signal conditioner, an analog to digital converter, and a notebook sized computer receiving digitized samples of the accelerometer signal and programmed to measure and calculate certain parameters from the digitized accelerometer signal; to provide such a system which can record and store a large number of data records including the digitally sampled impact hammer deceleration curves and parameters derived therefrom; to provide such a system which has the capability of deriving a full range of impact parameters in the field virtually immediately after each accelerometer signal is digitized; to provide such a system in which the field to be analyzed is divided into grid squares and the coordinates of the grid squares are entered into the data records of tests conducted on the grid squares, such that selected parameters of the testing procedure can be graphically mapped to show positional variations in the selected parameter over the area of the field under analysis; to provide such a system which is suitable for a wide range of soil surface testing applications; and to provide such a turf impact analysis system which is economical to manufacture, which is convenient and precise in use and operation, and which is particularly well adapted for its intended purpose.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a block diagram illustrating the principal components of a turf impact analysis system which embodies the present invention.

FIG. 2 is a diagrammatic side elevational view illustrating a Clegg impact hammer and guide tube for use in the turf impact analysis system of the present invention.

FIG. 3 is a block diagram illustrating the functional components of the turf impact analysis system in more detail.

DETAILED DESCRIPTION OF THE INVENTION

Figure 4:
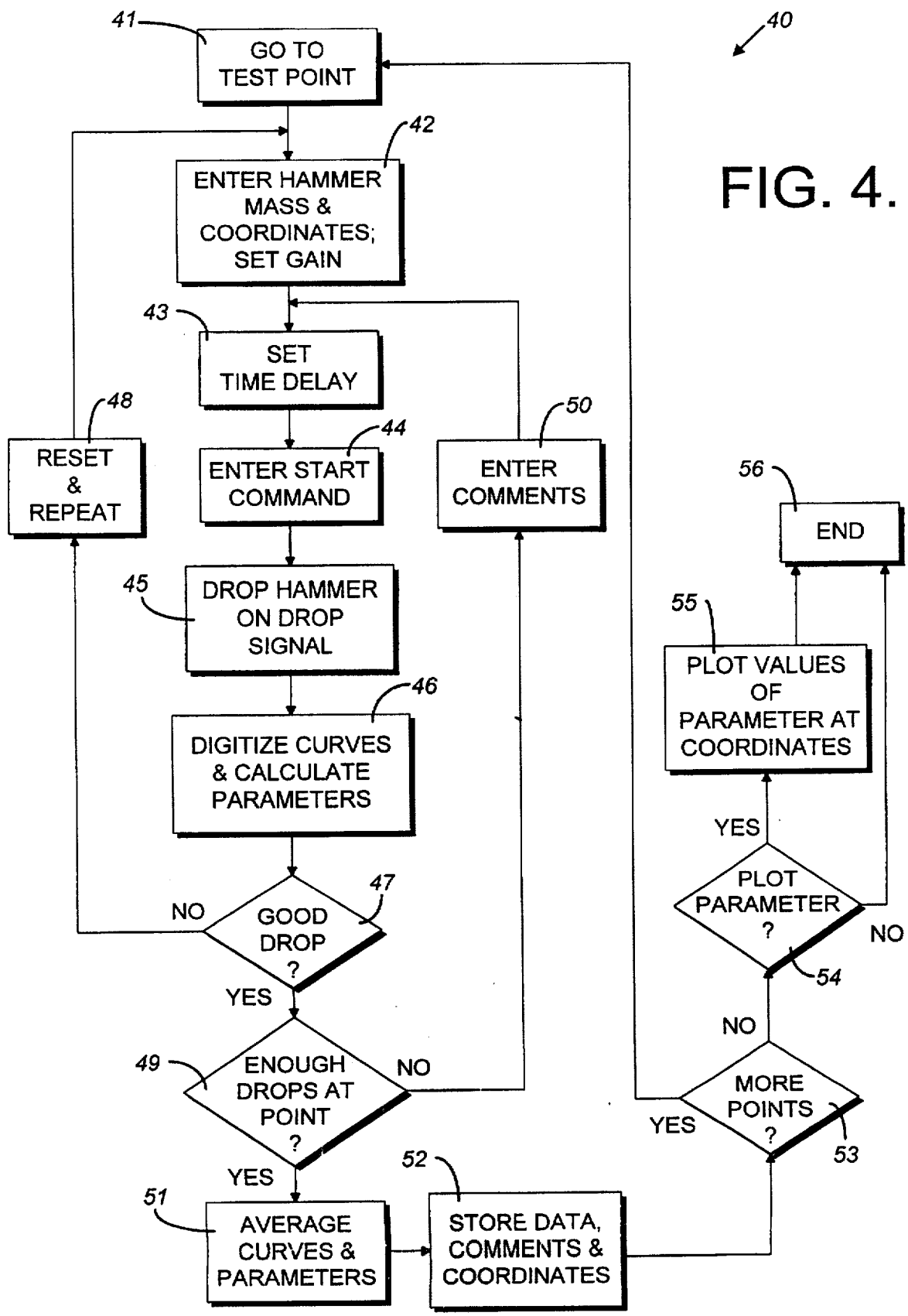
FIG. 4 is a flow diagram illustrating a method for conducting a turf impact analysis which embodies the present invention.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail:

The reference numeral 1 generally designates a turf impact analysis system which embodies the present invention. The system 1 generally includes a Clegg impact tester or Clegg hammer assembly 2 having an accelerometer 3 (FIG. 3) mounted therein, signal conditioner circuitry 4, data acquisition circuitry 5, and a notebook computer 6. The system 1 is used for gathering data about the nature of turf or soil surfaces by impacting the surface with the Clegg hammer assembly 2 and analyzing the deceleration curve generated by the accelerometer 3. The system 1 is lightweight and portable and has the processing power to derive and store a complete set of impact parameters in the field at each testing point.

Referring to FIG. 2, the Clegg hammer assembly 2 includes a Clegg hammer proper 10 and a guide tube structure 11. The guide tube structure 11 is formed by a cylindrical guide tube 12 and a base flange 13 which allows the guide tube structure 11 to be self-standing. The Clegg hammer 10 includes an impact body or missile 16 having a shaft 17 extending upwardly therefrom and terminating in a handle 18. The illustrated impact body 16 has a mass of one half kilogram, which is one of several "standard" Clegg hammer masses. Other standard hammers have masses of 4.5 and 2.25 kilograms, and such hammers may also be used in the present invention. Preferably, the guide tube 12 has a length to allow dropping the impact body 16 from a standard height of 45.7 centimeters (about 18 inches). Alternatively, guide tubes 12 to allow other drop heights may also be employed in the present invention. The guide tube 12 or the impact body 16 may have an index mark to allow mutual alignment thereof to set the proper release height. The accelerometer 3 is mounted within the impact body 16 of the Clegg hammer assembly 2 and is of the piezoelectric type. A Clegg hammer assembly 2, such as is used in the present invention, may be obtained from Lafayette Instrument Company of Lafayette, Indiana.

Referring to FIGS. 1 and 3, the signal conditioner circuitry 4 improves the signal to noise ratio of an analog voltage signal from the accelerometer 3 and filters noise therefrom. The illustrated signal conditioner 4 includes an amplifier or active filter 21 having the capability of operating at any of several gain settings which may be selected by the test operator using a gain set switch 22. The gain selected is determined principally from the type of turf being impact tested, but can also be affected by the mass of the impact body 16 and the drop height. The amplifier 21 is configured as a low pass filter to attenuate signal components arising from vibrations extraneous to the impact of the body 16 with the test surface and electrical or radio signals in the vicinity of the test site. The object of the signal conditioner circuitry 4 is to provide a clean deceleration signal within a desirable amplitude range.

The data acquisition circuitry 5 includes principally an analog to digital converter (ADC) 25 and timing control circuitry (not shown) to facilitate accurate gathering of impact data. The ADC 25 periodically samples the analog signal from the accelerometer 3, as conditioned by the circuitry 4, measures the signal or voltage amplitude, and converts the amplitude to a digitally coded value for each sample. A turf impact analysis program (not shown) executed by the computer 6 allows the test operator to enter a start command by way of a keyboard 26 which causes the ADC 25 to open a "drop window" after a set time delay, which is signaled to the operator by an audible drop signal. During the drop window, the ADC 25 is activated to sample and digitize an input signal. The drop window may be set for a selected duration, or ADC 25 may be set to sample the deceleration signal as long as it is greater than a selected threshold amplitude.

The preferred data acquisition circuitry 5 is packaged in the form of a PCMCIA card, also known as a PC-card, which interfaces to the computer 6 by way of a PCMCIA interface 27. PCMCIA is a computer industry standard for interfacing accessories, principally to notebook type computers, but also to desktop computers having the required interface. Such cards are about the size of a credit card, although thicker, with a specified connector for mating with a similar PCMCIA connector of the computer. Modems, network interface cards, some ROM based software, and RAM expansions are packaged as PCMCIA cards. The data acquisition card 5 used in the present invention is one of a series of similar cards, for various types of interfaces, which are manufactured by National Instruments Corporation of Austin, Tex.

The computer 6 is a lightweight portable computer which may be operated on a rechargeable battery. Such computers tend to weigh about seven pounds or less, including the battery (not shown). The illustrated notebook computer 5 has a color LCD screen 30 which folds over the keyboard 26, and has a hard disk drive 31 of at least several hundred megabytes for storage of programs and data. The computer 6 has a printer port for connection of a printer 32 thereto, preferably at least four megabytes of RAM, and a fast 486DX type processor. Such computers are widely available from many manufacturers and distributors. The portability and power of the notebook computer 6, along with the PCMCIA data acquisition card 5, enable a test operator to conduct impact tests with the hammer assembly 2 and derive a complete set of impact parameters on each of a plurality of test points at a site without returning to a laboratory to download digitized curve records for off-site analysis and derivation of impact parameters. The hard drive 31 allows a great number of data records to be stored from testing at a site. Such records can be offloaded to other media using a port on the computer 6 or a floppy drive (not shown) for further analysis or archiving purposes.

Referring to FIG. 4, a method 40 of practicing turf or soil surface impact analysis according to the present invention is illustrated. The system 1 is of such a portable nature and has sufficient computing power and storage capacity that the majority of steps comprising the method 40 can be practiced in the field. This enables the generation of an impact hammer deceleration curve and a complete set of impact parameters to be generated in the field for each impact test point immediately after the impact occurs. The impact parameters of interest in the present invention include the total duration of the impact, the time to reach maximum deceleration, the average deceleration, the rate of change of deceleration at several stages over the duration of the impact, the area under the curve of deceleration versus time or severity index, the peak force, the deformation of the surface, and the time for the surface to return to its original state or rebounding time.

The field to be analyzed is divided into an array of grids and given coordinates, such as rectangular coordinates. The components of the system 1 are positioned at the first test point at 41, and the mass of the hammer impact body 16 and gain setting are entered into the computer 6 along with the coordinates of the current grid at 42. At step 43, a time delay is entered which sets a delay between the entry of a start command at 44 by the test operator and the generation of a drop signal at 45. The time delay gives the operator time to raise the hammer 10 to the desired height within the tube 12. When the hammer 10 is dropped, a deceleration signal is generated by the accelerometer 3, which is digitized at 46 by the analog to digital converter 25, The impact parameters are then calculated and displayed, along with the deceleration curve, by the computer 6.

The display of the deceleration curve and calculated impact parameters immediately after the hammer drop allows the operator to decide at 47 if the impact was acceptable. A factor which could adversely affect the quality of a drop includes tilting of the guide tube 12 which would slow the descent of the hammer 10. Other factors could also be involved such as noise or vibrations in the vicinity of the analysis. If the drop is judged not acceptable, the currently generated curve and parameters are discarded, and impact analysis program is caused to prepare for another drop at 48, which branches the method back to step 42. If the drop was acceptable, a decision is made at 49 if enough drops have occurred at the current test point. It is known that multiple drops at the same point can cause variations in the shape of the deceleration curve and the impact parameters because of the effect of the hammer impact body 16 on the soil surface.

If additional drops are to be conducted at the current test point, any comments may be entered at 50, and the process is returned to step 43 for each additional drop. The grid coordinates may be entered as comments in a comment field of a data record of the impact analysis program. When a sufficient number of drops have been conducted at the current point, the deceleration curves and parameters may be averaged at step 51 and stored on the computer hard drive 31 at step 52. At step 53, a decision is made as to whether impact hammer drops are to be conducted at additional test points. If so, the operator moves components of the system 1 to the next test point and the process returns to step 41.

If the system 1 in the field includes the printer 32, once all the test points have been impact tested, a decision is made at step 54 whether to plot a selected parameter, such as the severity index. If so, the variation of the selected parameter in each grid can be printed or plotted at step 55 to show the variation over the entire field, and the process ends at step 56. If plotting the parameter is not desired, step 55 is bypassed, and goes directly to the end 56. The generated parameters can be subsequently printed, graphed, or plotted at a location other than the field under analysis.

Once the impact parameters have been calculated for every grid on the field, the owner, or a contractor, can then take whatever turf management steps are required to correct any undesirable characteristics of the soil surface. This may involve sodding, changing the sodding, compacting, aerating, or the like, depending on the nature of the undesirable characteristics.

It is to be understood that while certain forms of the present invention have been illustrated and described herein, it is not to be limited to the specific forms or arrangement of parts described and shown.

What is claimed and desired to be secured by Letters Patent is as follows:

1. A method for impact analysis of a soil surface of a plurality of divisions of a substantial ground area and comprising the steps of:

(a) dividing said ground area into an array of a plurality of location divisions;

(b) assigning each of said location divisions a set of location coordinates;

(c) at each of said location divisions, impacting said soil surface with an impact body having a selected mass, dropped from a selected height, and having an accelerometer mechanically coupled thereto which generates an analog signal corresponding to a deceleration curve which represents deceleration of said impact body over time upon impact with said soil surface at said location division;

(d) digitizing said analog signal at said location division to derive a digital representation of said analog signal using an analog to digital converter circuit;

(e) calculating a plurality of selected impact parameters including a severity index from said digital representation at said location division using a portable computer having a mass storage device and a computer display and having said analog to digital converter circuit interfaced thereto;

(f) digitally recording said digital representation, said selected impact parameters, and said location coordinates at said location division within said mass storage device of said computer;

(g) displaying said selected impact parameters and said deceleration curve on said computer display;

(h) repeating steps (c) through (h) at each location division until an acceptable set of said selected impact parameter and said deceleration curve are obtained for said location division; and (i) graphically mapping a corresponding one of said acceptable set of said selected impact parameters for each location division on a graphical representation of said ground area to display at least a two dimensional representation of a variation of said one of said selected impact parameters over said location divisions of said ground area.

2. A method as set forth in claim 1 wherein multiple soil impacts are performed at a particular location division and including the steps of:

(a) averaging corresponding ones of said selected impact parameters by said computer over said multiple soil impacts;

(b) recording average values of said selected impact parameters in said mass storage device;

(c) averaging deceleration curves generated by said computer over said multiple soil impacts; and (d) recording data representing an averaged deceleration curve for said particular location division in said mass storage device.

3. A method as set forth in claim 1 and including the steps of:

(a) entering a start command into said computer;

(b) clocking a drop delay time by said computer after entry of said start command; and (c) generating an audible drop signal at completion of said drop delay time to alert an operator to impact said soil with said impact body.

4. A method as set forth in claim 1 and including the steps of:

(a) coupling a signal conditioning amplifier with adjustable gain between said accelerometer and said computer; and (b) prior to impacting said soil at a location division, adjusting said gain of said amplifier according to a condition of said soil surface at said location division.

* * * * *